United States Patent [19]
Bellinga

[11] 3,950,136
[45] Apr. 13, 1976

[54] METHOD AND DEVICE FOR TAKING GAS SAMPLES

[75] Inventor: Hendrik Bellinga, Roden, Netherlands

[73] Assignee: N.V. Nederlandse Gasunie, Groningen, Netherlands

[22] Filed: Nov. 5, 1974

[21] Appl. No.: 521,136

[30] Foreign Application Priority Data
Nov. 7, 1973 Netherlands .................. 7315230

[52] U.S. Cl. .......... 23/232 R; 23/254 R; 73/421.5 R
[51] Int. Cl.² ........................................ G01N 1/22
[58] Field of Search .......... 23/232 R, 254 R, 255 R; 73/23 R, 24, 421.5, 422

[56] References Cited
UNITED STATES PATENTS

| | | | |
|---|---|---|---|
| 2,775,885 | 1/1957 | Rassweiler et al. | 73/24 |
| 2,785,567 | 3/1957 | Poole et al. | 73/24 |
| 3,429,186 | 2/1969 | Price et al. | 73/421.5 |
| 3,837,808 | 9/1974 | Sugimoto et al. | 23/232 E |

*Primary Examiner*—R. E. Serwin
*Attorney, Agent, or Firm*—Cushman, Darby & Cushman

[57] ABSTRACT

Method and apparatus for determination of the average composition of a gas under pressure over a certain period of time by regularly taking gas samples, which are stored in a collecting vessel. The gas is periodically led for a short, each time identical, length of time to the collecting vessel via a line in which a part is so dimensioned that, at a supercritical pressure ratio, a gas velocity occurs in it equal to the velocity of sound in the gas. In this way, all samples contain the same quantity of gas and a truly average sample is collected in the collecting vessel, as long as the pressure in the collecting vessel is less than about half the pressure upstream of said part.

9 Claims, 1 Drawing Figure

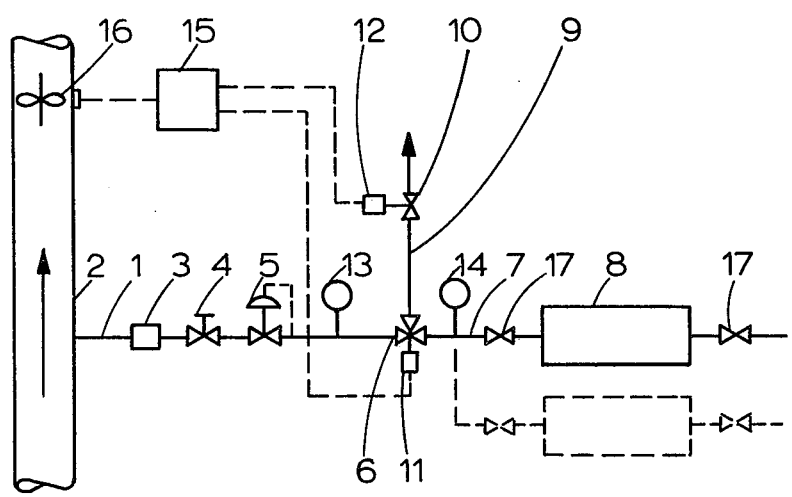

METHOD AND DEVICE FOR TAKING GAS SAMPLES

The invention relates to a process and a device for determination of the average composition of a gas under pressure over a certain period of time by regularly taking gas samples, which are stored in a collecting vessel.

A device for automatic implementation of the process referred to above is known from U.S. Pat. No. 3,429,186. This sturdy and rather simple device brings the disadvantage that the quantity of gas sample taken depends on the pressure of the gas to be sampled and on the accumulated pressure in the collecting vessel. As a result of this no exactly average sample is obtained.

Continuously operating gas-analysis equipment is also known. The equipment is vulnerable and calls for regular calibration. To obtain an average result, either calculatory work is to be done or the measuring data must be processed by supplementary calculating apparatus.

The object of the invention is to obtain a process which can be applied with use of simple, sturdy equipment and with the aid of which the average composition of the gas to be sampled can be determined at set times in a reliable way.

According to the invention this is achieved if for a short — each time identical — period of time part of the gas under pressure is periodically led via a line to the collecting vessel, in which line a part is so dimensioned that, at a supercritical pressure ratio, a gas velocity occurs in it which is identical to the sound velocity, whereupon when the collecting vessel is filled to a pressure less than half the pressure of the gas upstream of the element in which a gas velocity equal to the sound velocity occurs, the contents of the collecting vessel are analyzed.

It is essential in the case of the present process that the collecting vessel is filled with a number of, each time identical, gas quantities. This is based on the known principle indicating that if in a line section a supercritical pressure ratio occurs the gas velocity in this section becomes equal to the sound velocity and, hence, that the gas quantities passed through per unit of time are identical. This holds in so far as the end pressure (i.e. the pressure in the collecting vessel) is less than about half the pressure present before the line section in question.

A sample may be taken with regular time intervals. If samples are taken from a gas transport line with a fluctuating load the sampling frequency may be set to be proportional with the gas quantity transported. In this way a weighed average of the composition is obtained. By preference, it will be possible for the short period mentioned to last a fraction of a second; all this being dependent on the size of the collecting vessel. The period between the samplings may vary strongly and last from a few minutes up to several hours, which depends on the variations in the gas composition and/or the gas quantities. The system may, for instance, be so dimensioned that, at a sampling frequency of twice per hour, analysis of the contents of the collecting vessel need be carried out only once during 10 days if atmospheric pressure is started from. Of course, the composition of the initial contents of the collecting vessel must then be allowed for. It is also possible to start with an evacuated collecting vessel.

The invention also relates to a device for implementing the present process. The device is characterized by a line capable of supplying the gas to be sampled under pressure and connected with a collecting vessel that can be closed, in which line means are incorporated to either discharge the gas supplied or to pass it to the collecting vessel, whilst part of the connection is so dimensioned that a supercritical flow will occur if gas is admitted to the collecting vessel and means are present to lead gas to the collecting vessel at a given command after gas has been discharged through the line beforehand.

It is noted that from U.S. Pat. No. 3,699,814 a device is known for obtaining a continuous and constant flow of gas to be sampled, respectively sampling gas, in which a Venturi-shaped restriction is incorporated in the (sampling) gas line, and, downstream of the Venturi, a fan having such a capacity that a supercritical pressure ratio occurs across the Venturi. This concerns a system, therefore, in which a constant flow of gas to be sampled is taken off continuously, contrary to the process and the device according to the invention, in which each time equal, discrete quantities of gas to be sampled are stored in a collecting vessel.

The device according to the invention is preferably used to sample the gas in transport lines, for instance for the purpose of determining the composition and the calorific value of the gas transported. A non-limiting embodiment of the device, shown in the pertaining drawing, consists of a connecting line 1, which is in connection with the gas under pressure in a transport line 2, whilst in connecting line 1 are incorporated successively: a dust filter 3, a valve 4, a reducing valve 5 and a three-way valve 6 the first outlet channel 7 of which is connected with the collecting vessel 8 and the second outlet channel 9, provided with a valve 10, ends up freely, the passage of the three-way valve 6 to the first channel 7 and the second channel 9 being so dimensioned that during the flushing and during the filling of the collecting vessel 8 a supercritical pressure ratio occurs, whilst the three-way valve 6 and the valve 10 are provided with means 11 and 12 in order to lead gas to the collecting vessel 8, respectively to discharge it and to shut it off, at a command given. Valve 10 must be so dimensioned that the pressure in line 9, if valve 10 is opened, is lower than half the pressure read on pressure gauge 13. The function of the reducing valve 5 is to keep the pressure constant before the supercritical flow section. The valves 6 and 10 have the following function: when in rest condition, three-way valve 6 is in the position for venting, whilst valve 10 is closed. A filling command first opens valve 10 to fill the line 1, by discharge, with the gas to be sampled. Next, three-way valve 6 is placed in the filling position for a short time, so that line 1 is connected with channel 7, for instance for a fraction of a second, whilst simultaneously, or shortly thereafter, valve 10 is closed. Said sampling is thereby completed.

It goes without saying that the device may be provided with pressure gauges 13 and 14 to check for proper performance, particularly to check for the required difference between the pressure after the reducing valve 5 and the pressure in the collecting vessel(s) 8. The means 11 and 12 for operation of the valves 6 and 10 may be solenoids connected to a control unit 15. The control unit may emit impulses at regular time intervals, or impulses proportional to the gas quantity transported via line 1, for instance with the aid of a turbo-meter 16. Operation may also be effected pneumatically or hydraulically for that matter. If necessary, several collecting vessels 8, provided with valves 17, may be connected in parallel, in which case they are filled to the maximum permissible pressure one by one or simultaneously, notably to half the set pressure of reducing valve 5.

What is claimed is:

1. Process for obtaining a composite sample of average composition of a gas in a gas sample collecting vessel which process comprises providing a gas under pressure, providing a gas sample vessel for receiving said gas and a means for directing said gas into said gas sample collecting vessel, feeding said gas through said means into said gas sample vessel; wherein the pressure drop of said gas through said means is such that the gas travels through said means at a velocity equal to the velocity of sound within said gas; filling said sample collecting vessel so that the pressure within said sample collecting vessel does not exceed half the pressure upstream of said means, whereby a truely average sample of said gas is collected in the gas sample collecting vessel.

2. Process for obtaining a composite sample of average composition of a gas in a gas sample collecting vessel which process comprises providing a gas under pressure, providing a gas sample vessel for receiving said gas and a means for directing said gas into said gas sample collecting vessel, feeding said gas through said means into said gas sample vessel, wherein the pressure drop of said gas through said means is such that the gas travels through said means at a velocity equal to the velocity of sound within said gas; filling said sample collecting vessel so that the pressure within said sample collecting vessel does not exceed half the pressure upstream of said means, comprising the further step of directing said gas into said sample collecting vessel during short, identical periods of time at regular time intervals.

3. Process according to claim 2, wherein said means is a channel or a bore of a valve, said gas passing through said channel into said collecting vessel.

4. Process according to claim 2 in which said short identical periods of time are less than one second.

5. Process for obtaining a composite sample of average composition of a gas taken from a gas transport line in a gas sample collecting vessel which process comprises taking a gas under pressure, from a gas transport line, providing a gas sample vessel for receiving said gas and a means for directing said gas into said gas sample collecting vessel, feeding said gas through said means into said gas sample vessel, wherein the pressure drop of said gas through said means is such that the gas travels through said means at a velocity equal to the velocity of sound within said gas, filling said sample collecting vessel so that the pressure within said sample collecting vessel does not exceed half the pressure upstream of said means, comprising the further step of directing samples of said gas into said sample collecting vessel during short, each time identical, periods of time at a sampling frequency which is proportional to the gas quantity transported in said gas transport line.

6. Process according to claim 5, in which said short identical periods of time are less than one second.

7. An apparatus for obtaining composite samples of average composition from a gas under pressure in a vessel or a gas transport line, comprising a conduit having a first section to be placed in open communication with said vessel or gas transport line and a second section to be placed in open connection with a gas sample collecting vessel, valve means in said conduit intermediate said first and second sections, which in a first operative position connect said first section to said second section and in a second operative position connect said first section to gas discharge means, a restriction in said conduit, so designed that supercritical flow occurs in said restriction when said valve means are in said first operative position and the pressure upstream of said restriction is more than two times the pressure in said gas sample collecting vessel and control means to place said valve means alternatingly in said first and second operating positions.

8. An apparatus for obtaining composite samples of average composition from a gas under pressure in a vessel of a gas transport line comprising a conduit having a first section to be placed in open communication with said vessel or gas transport line and a second section to be placed in open connection with a gas sample collecting vessel, a three-way valve in said conduit intermediate said first and second sections, which in a first operative position connects said first section to said second section and in a second operative position connects said first section to a gas discharge tube, a shut-off valve in said gas discharge tube, the bore of said three-way valve which is operative in said first operative position forming a restriction in said conduit, so designed that supercritical flow occurs in said restriction when said three-way valve is in said first operative position and the pressure upstream of said three-way valve is more than two times the pressure in said gas sample collecting vessel, and control means to place said three-way valve alternatingly in said first and second operating positions and to open and close said shut-off valve.

9. An apparatus for obtaining composite samples of average composition from a gas under pressure in a gas transport line, comprising a conduit having a first section to be placed in open communication with said gas transport line and a second section to be placed in open connection with a gas sample collecting vessel, a three-way valve in said conduit intermediate said first and second sections, which in a first operative position connects said first section to said second section and in a second operative position connects said first section to a gas discharge tube, a shut-off valve in said gas discharge tube, the bore of said three-way valve which is operative in said first operative position forming a restriction in said conduit, being of a dimension which causes a supercritical flow in said restriction when said three-way valve is in said first operative position and the pressure upstream of said three-way valve is more than two times the pressure in said gas sample collecting vessel, control means to place said three-way valve alternatingly in said first and second operating positions and to open and close said shut-off valve, and a flow meter in said gas transport line providing a flow signal to said control means for setting the operating frequency of said control means.

* * * * *